United States Patent
Scheuering

(10) Patent No.: US 9,615,804 B2
(45) Date of Patent: Apr. 11, 2017

(54) METHOD FOR IMAGE GENERATION AND IMAGE EVALUATION

(75) Inventor: Michael Scheuering, Nuremberg (DE)

(73) Assignee: Siemens Aktiengesellschaft, Munich (DE)

(*) Notice: Subject to any disclaimer, the term of this patent is extended or adjusted under 35 U.S.C. 154(b) by 801 days.

(21) Appl. No.: 13/531,841

(22) Filed: Jun. 25, 2012

(65) Prior Publication Data

US 2013/0004037 A1    Jan. 3, 2013

(30) Foreign Application Priority Data

Jun. 29, 2011    (DE) .................... 10 2011 078 278

(51) Int. Cl.
| | |
|---|---|
| G06K 9/62 | (2006.01) |
| A61B 6/00 | (2006.01) |
| G06F 19/00 | (2011.01) |
| G06T 11/00 | (2006.01) |
| A61B 6/03 | (2006.01) |

(52) U.S. Cl.
CPC .......... *A61B 6/5205* (2013.01); *A61B 6/5294* (2013.01); *G06F 19/321* (2013.01); *G06F 19/345* (2013.01); *G06T 11/006* (2013.01); *A61B 6/032* (2013.01); *A61B 6/468* (2013.01)

(58) Field of Classification Search
None
See application file for complete search history.

(56) References Cited

U.S. PATENT DOCUMENTS

| | | | | |
|---|---|---|---|---|
| 4,835,690 A | * | 5/1989 | Gangarosa | G01R 33/54 324/318 |
| 6,901,130 B2 | | 5/2005 | Bruder et al. | |
| 7,848,936 B2 | | 12/2010 | Glaser-Seidnitzer et al. | |
| 7,903,859 B2 | | 3/2011 | Boeing et al. | |
| 8,000,510 B2 | | 8/2011 | Boeing et al. | |

(Continued)

FOREIGN PATENT DOCUMENTS

| | | |
|---|---|---|
| DE | 10 2007 030 068 | 1/2009 |
| DE | 10 2010 009 105 | 8/2011 |
| WO | 2010/131131 | 11/2010 |

OTHER PUBLICATIONS

Yu, Lifeng, et al. "Automatic selection of tube potential for radiation dose reduction in CT: a general strategy." Medical physics 37.1 (2010): 234-243.*

(Continued)

*Primary Examiner* — Vikkram Bali
*Assistant Examiner* — Tracy Mangialaschi
(74) *Attorney, Agent, or Firm* — Schiff Hardin LLP

(57) ABSTRACT

In a method for image generation and image evaluation in the medical field, raw data are generated by a selected medical modality, in particular a computed tomography scanner, depending on given modality parameters, and image data are generated from the raw data using an image reconstruction depending on given reconstruction parameters. The image data are evaluated by a given analysis application. Before acquiring the raw data, a secondary application automatically proposes a set of parameter values for the modality parameters and/or for the reconstruction parameters coordinated to the given analysis application and/or given patient information.

13 Claims, 2 Drawing Sheets

(56) References Cited

U.S. PATENT DOCUMENTS

| | | | |
|---|---|---|---|
| 2004/0082846 A1* | 4/2004 | Johnson | A61B 5/02014 600/410 |
| 2005/0100201 A1* | 5/2005 | Mayer et al. | 382/128 |
| 2005/0267348 A1* | 12/2005 | Wollenweber et al. | 600/407 |
| 2007/0165930 A1* | 7/2007 | Feuerlein | 382/128 |
| 2008/0044069 A1* | 2/2008 | DuGal | 382/128 |
| 2008/0310698 A1* | 12/2008 | Boeing et al. | 382/131 |
| 2009/0279672 A1* | 11/2009 | Reiner | A61B 6/583 378/207 |
| 2009/0290773 A1* | 11/2009 | Holt | G06F 19/321 382/131 |
| 2010/0040268 A1 | 2/2010 | Boeing et al. | |
| 2010/0183206 A1* | 7/2010 | Carlsen et al. | 382/128 |
| 2012/0046971 A1* | 2/2012 | Walker et al. | 705/3 |

OTHER PUBLICATIONS

Heinz Morneburg Bildgebende Systems für die medizinische Diagnostik (Hrsg.) vol. 3, Munich, Publicis-MCD-Verlag, ISBN 3-89578-002-2, pp. 141-145; Book; 1995; DE.

\* cited by examiner

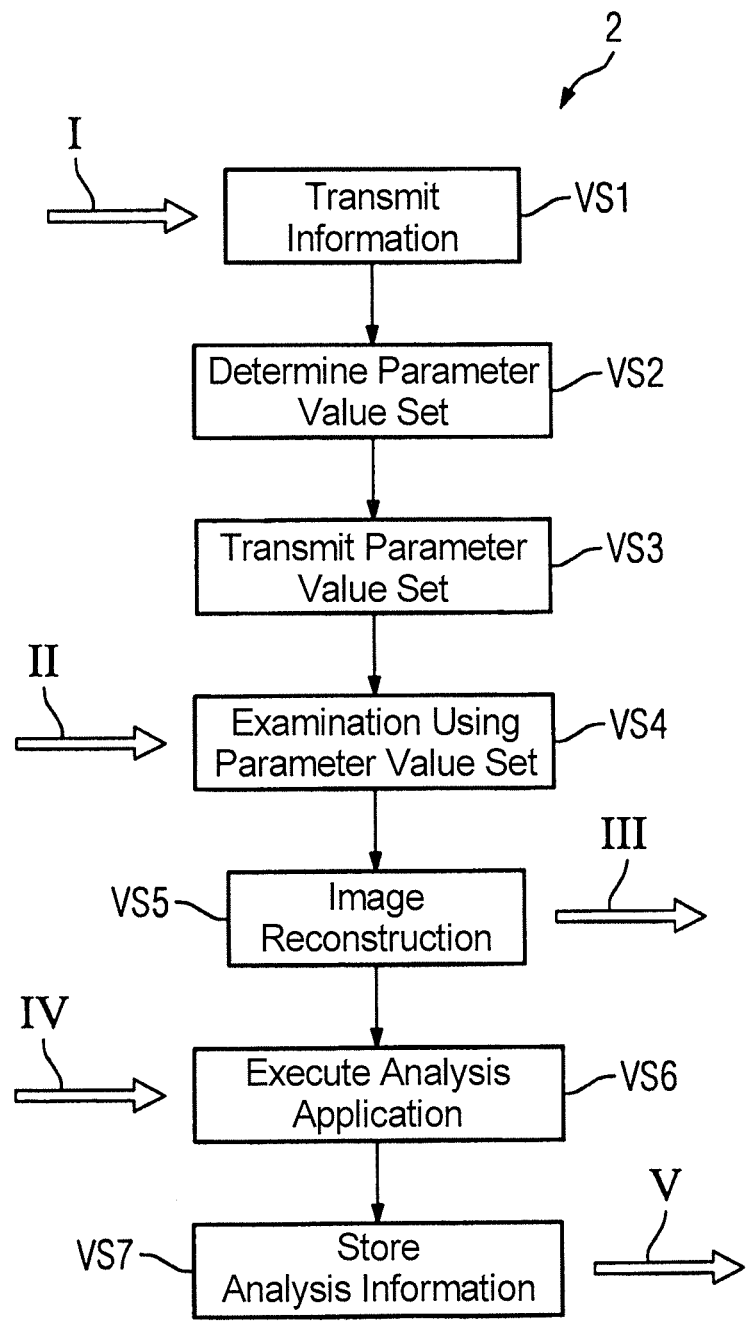

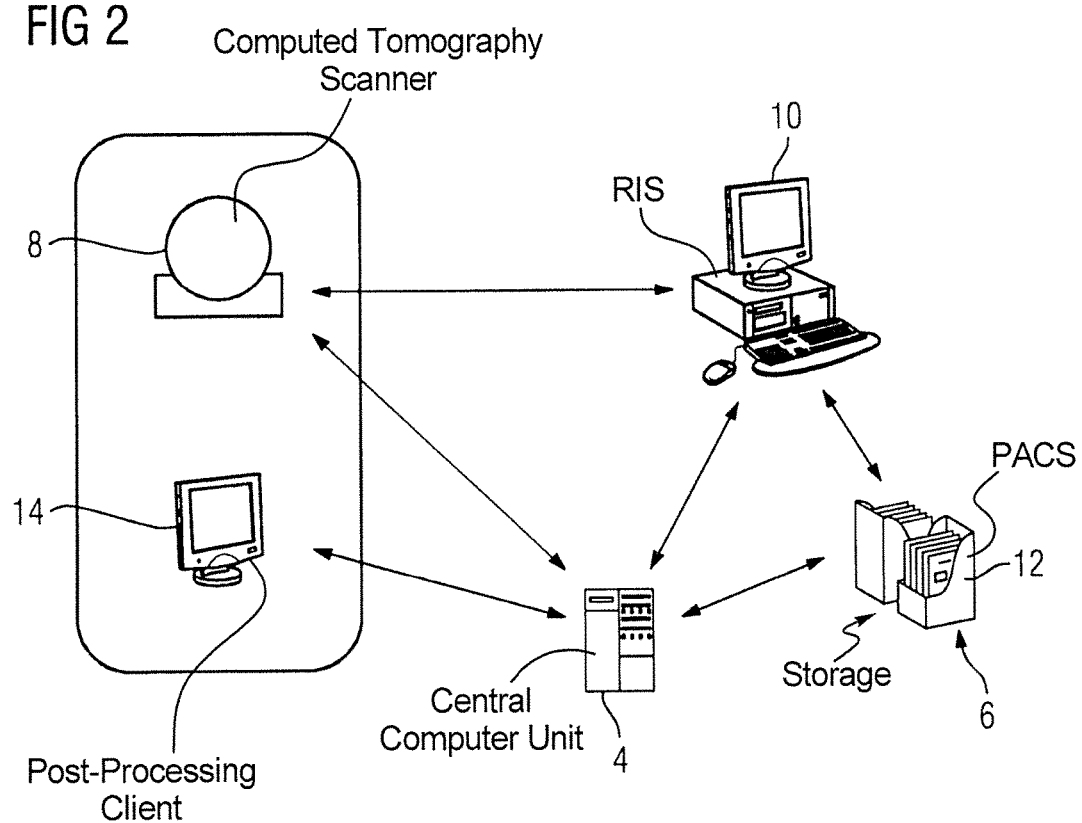

METHOD FOR IMAGE GENERATION AND IMAGE EVALUATION

BACKGROUND OF THE INVENTION

Field of the Invention

The invention concerns a method for image generation and image evaluation in the field of medicine, wherein raw data are generated by means of a given medical modality, in particular a computed tomography scanner, depending on given modality parameters, and wherein image data are generated by an image reconstruction, depending on given reconstruction parameters, and wherein the image data are evaluated by means of a given analysis application.

Description of the Prior Art

In modern medicine, examinations are implemented with the use of an imaging modality, in order to make a diagnosis based on the results of an examination of this type, or to verify a diagnosis. The modalities used for this, such as a computed tomography scanner, for example, are continuously improved thereby, and as a result additional application possibilities arise, and the obtainable results are improved.

As a result, computed tomograph scanners, for example, are used and further developed meanwhile, which function with non-monochromatic X-rays. Corresponding examination procedures are frequently referred to as Dual-X-Ray-Absorptiometry, or Dual-Energy-X-Ray-Absorptiometry, abbreviated as DXA, or DEXA. They are suited for, among other things, osteodensitometry, i.e. bone density measurement.

Moreover, computed tomograph scanners are currently used, for example, in which the image generation in the framework of a heart examination, i.e. in a so-called cardio CT, is coordinated with the heartbeat of a patient. This means that the image generation, or the generation of raw data, always takes place during a relatively quiet phase, toward the end of the heartbeat. With the use of this so-called "step-and-shoot-method," it is possible, in particular, to reduce blurring due to movement.

Furthermore, due to the constant development work, the number of analysis applications is increasing, which should support a physician in the evaluation of the obtained information. As such, a program for image evaluation is being developed currently, that recognizes potential problematic structures, and highlights said structures in color in a corresponding image depiction. This program is intended in particular for CT colonoscopy, i.e. basically a colonoscopy by means of computed tomography, and should alert the physician of possible polyps, for example.

Common modalities and functionality are known to those skilled in the art as a matter of principle. In the case of a computed tomography scanner, the functional basis of, for example, spiral computed tomography, is described in, among others, the books, "Computertomographie" [Computer Tomography] (ISBN 3-89-578-082-0, chapter 3) and "Bildgebende Systeme für die medizinische Diagnostik" [Image Generating Systems for Medical Diagnosis] (ISBN 89578-002-2, chapter 5.5). Generally, the modalities first generate raw data, which typically is subsequently, thoroughly processed with software. Advantageous methods for a first processing of raw data are presented, for example, in DE 10 2006 002 037 A1 and DE 102 38 322 A1.

In the course of further development of the modalities and the software pertaining thereto, the technical demands placed on the modalities and the software, and thus the complexity thereof, are inevitably increasing. For a most effective use, it is necessary that the respective modality as well as the respective software be individually coordinated to each individual examination. To implement an appropriate coordination, it is possible for a user to vary numerous parameters for the respective examination. There are thus numerous configuration possibilities available for the modality, as well as the respective software. The configuration possibility selected for an examination determines the quality of the information obtained by means of that examination.

Unfortunately, there are normally multiple different modalities for medical apparatuses, which differ with respect to the type of apparatus, the model, and with respect to the manufacturer, and these modalities may combine various software packages with one another, or use the software packages in parallel. Furthermore, the modalities and software packages are frequently from different manufacturers, so a software package may then not be compatible with a specific modality, but ideally should be compatible with as many modalities as possible.

There are presently two basic problems with achieving this ideal situation. Firstly, the coordination of the modality and the software to a respective examination is currently only able to be done to an approximate degree, and is substantially based on a few of the user's empirical values. Secondly, the number of configuration possibilities increases the risk that, inadvertently, a less favorable configuration possibility is selected.

SUMMARY OF THE INVENTION

An object of the invention is to provide an improved method for image generation and image evaluation.

The desired improvement is obtained in accordance with the invention by, firstly, appropriate additional information, specifically information regarding the intended image evaluation, is taken into account for the selection of an advantageous configuration possibility for a modality and associated software, and secondly, the selection is carried out systematically and in a reproducible manner, based on stored data. In this manner, it is possible to obtain a more precise coordination for each examination, i.e. a fine-tuning of the modality and the associated software.

For this purpose, in accordance with the invention a secondary application, available as evaluation software, for example, automatically makes a proposal to the operator of a set of parameter values, coordinated to a given analysis application and/or given patient information of the patient, that characterizes exactly one configuration possibility for the modality as well as the associated software. This configuration possibility is then used for an examination of the patient, by means of which the individual technical substeps of the procedure, i.e. the generation of raw data by means of a given medical modality, depending on given modality parameters, the generation of image data from the raw data with the aid of an image reconstruction, depending on given reconstruction parameters, and in particular, the analysis of the image data by means of a given analysis application, are precisely coordinated to one another. The set of parameter values contains parameter values for the modality parameters and for the reconstruction parameters. Because a physician normally is interested, in particular, in the information that will be obtained through the analysis application, the parameter values are selected such that the image data obtained in the framework of the examination are particularly well suited to the selected analysis application.

An examination that is coordinated or parameterized in this manner in advance, in which, in particular, the technical procedural steps for executing the intended image evaluation are also taken into consideration, can be designed, at least in relation to the results, substantially more effectively. The information obtained thereby offers therefore an improved basis, based on which the physician eventually makes a diagnosis, or verifies a diagnosis. Through the use of the secondary application, it is furthermore made substantially easier for the user/operator to make a selection of an appropriate and advantageous coordination of the individual technical procedural steps to one another for each individual examination.

The method described comprehensively below serves for image generation and image analysis in the medical field, and is accordingly provided for generating information based on which a medical diagnosis is made or verified. In the preparation of the actual examination, an examination method coordinated to the patient and the patient's clinical picture is first provided by the physician. This is established therefore, through the modality with which the patient is to be examined, and the patient's body region in question, in order to optimize a particular result such as, for example, the image sharpness of the examination.

A "modality" means, for example, a computed tomography scanner, a magnetic resonance tomography scanner, or an ultrasound apparatus.

In addition to this, the physician, or in some cases, the technician trained for the intended modality, selects from among numerous available analysis applications (also referred to as post-processing applications), an analysis application that is advantageous for the present case, and therefore for the upcoming examination. An analysis application of this type concerns an algorithm, normally in the form of software, that can be executed by a computer. Using an appropriate analysis application, image data generated in the framework of the procedure are processed, by means of which the evaluation of the obtained information can be substantially more easily coordinated by the physician.

For example, analysis applications are available that identify raw data and/or image data that originated from uric acid crystals, and highlight in color the corresponding region in an image that has been generated. Based on the distribution of the color coding of an image of this type, the physician then decides whether or not gout is present as the result of uric acid crystal deposits. The effectiveness and precision of an analysis application of this type depends, however, on the style and manner with which the raw data and/or image data are generated. This means that the parameter values selected for the modality parameters and for the reconstruction parameters have an effect on the effectiveness and precision of the analysis application. Therefore, the parameter values are coordinated, in particular, to the intended analysis application as well, because the information that is obtained thereby is normally dependent on the image sharpness desired by the physician.

The examination method given by the physician, i.e. the selected modality, the body part of the patient that is to be examined, and the selected analysis application, as well as the interest in further patient information, in particular patient specific information, function in the framework of the method as the basis information for a secondary application, and are therefore supplied to this secondary application.

In the next step of the inventive method, the secondary application automatically proposes a set of parameter values based on the basis information, and in particularly, based on the given analysis application and/or given patient information, which determines the style and manner of image generation and image evaluation, i.e. the details of the examination of the patient. The user, usually a medical technical assistant, (MTA) of the modality then decides whether to use the proposed parameter values, coordinated to the given analysis application and preferably to other known patient information, or whether to vary individual parameter values for the examination, according to his or her own discretion. In other words, at this point, a configuration possibility, characterized by the parameter values, specific to the modality and associated software, is selected. The secondary application is preferably executed as software, and the user confirms the use of the proposed parameter values for the examination by means of, for example, pressing a button.

If the parameter values are given by the user, preferably through confirming the proposed parameter values, then subsequently the actual examination of the patient is started, wherein raw data are generated by the operation of the given medical modality, such as a computed tomography scanner, in dependence on the modality parameters. Image data are generated from the raw data using an image reconstruction dependent on given reconstruction parameters, and the image data are then evaluated by means of the selected analysis application. Parameter values for the modality parameters, as well as for the reconstruction parameters, are contained in the proposed set of parameter values, such that all sub-steps during the image generation and image evaluation are coordinated to one another by the secondary application. As a result, the yield of a corresponding examination method is increased, and the information obtained with the analysis application is refined.

If, for example, a patient suspected of having a tumor in a specific region of the body is to be examined using a computed tomography scanner, and an analysis application has been selected, which automatically determines raw data and/or image data that are typical of tumor tissue, and performs a determination, based on the data obtained in this manner, for the expansion of the suspected tumor tissue, the secondary application automatically proposes parameter values, dependent on this analysis application, for the computed tomography scanner and its software, such that the determination of the expansion of the suspected tumor tissue is carried out by means of the analysis application, with the highest possible degree of precision.

In this example, a computed tomography scanner, including software for image reconstruction, is provided, as is known to those skilled in the art. With an appropriate computed tomography scanner, parameter values are typically available as parameters, such as, for example, for configuring a primary or secondary collimator, for the scanning mode, i.e. spiral scan, or scanning according to the step-and-shoot method, for example, the length of time of the scanning process, the speed of the scanning process, etc. These parameters also include, in accordance with the invention, modality parameters for the method. Accordingly, the reconstruction parameters in the case example depicted here indicate parameters for which, in particular, a value input is provided in the software for the image reconstruction. The convolution kernel, the pitch factor, or a suitable grey scale window, for example, are selected by means of a value input of this type.

According to an embodiment of the method, the analysis application is selected from a limited and, in particular, manageable number of analysis applications. The user therefore has different possibilities available for the analysis of the image data. Depending on the selected analysis application, the secondary application determines the parameter values coordinated to this selected analysis application. A parameterization, depending on the demands of the analysis algorithm, therefore results therefrom.

In addition, the analysis applications are consolidated in a software package, and in particular, designed as PC compatible programs. As a result, it is possible for a physician, for example, to execute the analysis application on a PC in an examination room, independently of the modality and, independently of the location, of the modality. It is further preferred that an interface having a pyramid-like, ramifying selection structure is provided for the selection of the analysis application. This means that, for example, first the selection of the modality with which the raw data is generated, is carried out. Next, for example, the selection of the region to be examined, i.e. the head, torso, arms or legs, for example, is carried out. In the case of the selection of the torso, the selection of the individual organs is next, and in this case, separately developed analysis applications are available for each organ, such as, for example, a size measurement. With a selection structure of this type, the selection is made by the user intuitively, which is favorable from the point of view of the comfort level of the user, and there is the advantage that the physician, who typically selects the analysis method, only needs to be concerned with the branch of the selection structure covered by his or her field of specialization. For an orthopedic specialist, it is therefore sufficient for him or her to be concerned with analysis methods for the examination of the skeleton or joints, and for the neurologist, it is sufficient to concern himself or herself with analysis methods suitable for the examination of the nervous system.

Although each analysis application executes a specific analysis substantially automatically, it is provided that the user of the analysis application is allowed certain liberties for affecting the analysis application, such that the user can preset or readjust the contrast, brightness or color, in a manner similar to that of a program for processing photographs, for example.

A very advantageous selection of analysis applications contains an analysis application for segmenting the image data as well. Segmentation normally refers to a sub-category of digital image processing. The goal of segmentation is the generation of interrelated regions, with respect to the content, in an image composed of pixels or voxels, wherein the regions are created by combining neighboring pixels or voxels on the basis of a previously determined homogeneity criterion. The most commonly used methods for automatic segmenting of images are the pixel oriented method, edge oriented method, texture oriented method, and the model based method. Through the use of this segmenting, it is possible to determine pixels or voxels within an image, for example, having a data basis that is typical for tumor tissue, and depicting said tissue in a coherent and optically highlighted cluster. It is then substantially easier for the physician to determine whether this is a tumor and how large it is.

In another embodiment, the selection of analysis applications also includes an analysis application for the automatic analysis of segmented image data. An analysis application is thus provided with which, for example, an automatic measurement is carried out of a region that is coherent with respect to the content. In the above-described example of a suspected tumor, an analysis application of this type consequently gives the dimensions and in particular, the largest expansion of the potential tumor.

In a preferred embodiment, the secondary application proposes suitable parameter values based on contrast or image sharpness requirements for the given analysis application. In this case, variables such as image sharpness and noise are taken into account, which, in an image reconstruction, i.e. in the conversion of the raw data into image data, typically cannot be modified independently of one another. Depending on the analysis application that has been selected, an emphasis is therefore placed on these values that is advantageous for the analysis application by means of the parameter values. If, for example, a potential tumor is to be measured in a lung, then the inner structure of the tumor is not the primary interest, for which reason a set of parameter values is selected that results in a highlighting of edges and thereby a highlighting of the surface of the suspected tumor. By highlighting the edges in an image, the highlighted image is then better suited for the execution of an analysis application for size measurement based on the highlighting. If instead, the structure of the tumor should be depicted, then a set of parameter values is selected that results in the greatest possible image sharpness, even if, as a result, the transition to neighboring tissues cannot be as easily identified, due to noise. An image optimized in this manner is suited, for example, to an analysis application which highlights, in color, regions having a density that exceeds a threshold.

According to a preferred variation of the method, the modality parameters are preset automatically by the secondary application. Analogously, a method is also preferred in which the reconstruction parameters are automatically preset by the secondary application. In both cases, and in particular through the combination of both variations of the method, the ease of use is significantly increased. The user confirms, preferably through the pressing of a button, the preset parameter values, and thus, initiates the actual examination of the patient. Aside from increasing the ease of use, the operational security is also increased, as potential input errors of parameter values are effectively prevented.

With the selection of suitable parameter values by means of the secondary application, preferably additional patient information is taken into account. Patient specific data can be provided as the patient information. Patient specific data are, for example, weight, height, and the patient's gender. Patient specific information of this type are necessary, for example, for determining a pathological increase or decrease in the size of an organ of the patient. For this purpose, therefore, a measurement of the size of the organ in relation to the size of the patient is implemented.

Information for an examination that has been carried out, which may include the parameter values as well, is stored preferably in a file; more preferably, in a file together with the image data, and thereby archived. In this manner it is possible to later reproduce the style and manner of the examination administered to the patient. If an examination archived in this manner concerns a first or a baseline examination, and a follow-up examination is planned, then, if desired, a portion of the information from the file on the baseline examination is taken into consideration by the secondary application in the determination of a suitable set of parameter values for the follow-up examination. In this manner, a good comparability between different examinations is created, in particular if the examinations are carried out in the same style and manner. A "follow-up" scenario of this type serves as a follow-up monitoring, among other things, for tumors. With numerous, temporally offset, but substantially identical, examinations, it is possible to determine whether a tumor has grown, or become stagnant.

Likewise, a "follow-up" scenario, as such, is suitable for checking whether or not deposits in a coronary artery can be removed by means of a medicinal treatment. With follow-up monitoring of this type, the person skilled in the art refers to the initial examination typically as a baseline scan, and the subsequent examination as a follow-up scan.

According to another embodiment of the method, a transformation of the set of parameter values for the baseline scan into the set of parameter values for the follow-up scan is obtained via the secondary function by means of a filed (memory accessible) algorithm. For this the follow-up scan is coordinated to the baseline scan for achieving a good comparability. A parameter value transformation of this type is useful, for example, if the baseline scan and the follow-up scan take place in different medical apparatuses. In this case, computed tomography scanners, for example, may be used for the scanning that are different regarding the model or manufacturer. In order to allow the examinations to take place with the greatest degree of freedom possible, in the same style and manner, a transformation or conversion of the parameter values is carried out, because the parameter values typically have different effects with different models. In this manner, the patient can decide in favor of a medical examination without needing to fear that the design of the medical apparatus may have a negative effect on the results of the examination with respect to comparability.

Furthermore, a variation of the method is advantageous, wherein the algorithm compensates in part for patient specific changes that take place between the baseline examination and the follow-up examination. If, for example, the patient's weight has decreased due to chemotherapy, then for the follow-up examination, the set of parameter values from the baseline scan are modified in such a manner that despite the weight change, a reasonable comparability is ensured. An analogous modification of the parameter values is also provided, for example, if the patient is still growing, and has changed size for that reason between the baseline scan and the follow-up scan. The consideration of a change in size is also, among other things, significant if, for example, as described above, a pathological enlargement or shrinkage of an organ is to be monitored.

In addition, it is useful for the algorithm to compensate in part for technical changes that take place between the baseline scan and the follow-up scan. In this regard, not only is the fact taken into account that a previously-used medical apparatus may be replaced with new medical modalities over time, but also, that typically an updating of the medical modality, i.e. a computed tomography scanner, for example, takes place at regular intervals. By using a transformation algorithm of this type, the secondary application functions particularly effectively and can also be implemented in a flexible manner.

In another embodiment, the secondary application is executed as a program on a central computer unit having a storage capacity, with the central computer being connected for the transfer of signals to numerous medical modalities for the controlling of said. Depending on the available basis information, the secondary application then determines a set of suitable parameter values, and transmits them to the medical modality intended for the examination.

BRIEF DESCRIPTION OF THE DRAWINGS

FIG. 1 is a flow chart of an embodiment of the method according to the present invention.

FIG. 2 schematically illustrates a configuration of components in accordance with the present invention, in an embodiment for executing the embodiment of the method shown in FIG. 1.

DESCRIPTION OF THE PREFERRED EMBODIMENTS

Components corresponding to one another have the same reference symbols in all figures.

The method 2 serves for image generation and image evaluation in the medical field and is accordingly provided, in order to generate information, based on which a physician can make a medical diagnosis for a patient, or verify a diagnosis. It is equally suited for a first or baseline examination and for a follow-up examination. The term follow-up examination in this case refers in the following to examinations, the results of which are to be compared with the results of the baseline examination. In order to achieve good comparability, it is advantageous, to execute the baseline and follow-up examinations in the same style and manner.

The method 2 shall be explained in the following in an exemplary manner using a case example, subdivided, as depicted in FIG. 1, into seven procedural steps VS1-VS7. In the first procedural step VS1, information is transmitted to a central computer unit 4, which files that information as basis information in a local memory. The transmitting of the information, symbolized by an information flow arrow I, takes place, for example, through an entry via an interface or by means of a data transfer between the central computer unit 4 and a separate data storage unit 6.

Typically, patient information, such as the size, weight and gender of the patient, for example, serves as the basis information. This patient information is entered by a physician in the case example, on a PC in an examination room, and sent to the central computer unit 4 as a file. In addition, said file contains the method determined by the physician for the examination, in this case an examination of the lower torso region of the patient by means of a computed tomography scanner 8, the analysis application selected by the physician, in this case the determination of the size of a suspected tumor, and the information that the upcoming examination is a follow-up examination.

Because it concerns a follow-up examination, a secondary application stored as a program on the central computer unit 4 accesses the information memory 6 and uploads all of the information from the relevant baseline examinations stored therein to the memory of the central computer unit 4. If the examination does not concern a follow-up examination, or none of the previous examinations are to be taken into consideration, then the secondary application simply skips over this step.

Based on the basis information collected and made available in this manner, the secondary application determines, in a second procedural step VS2, a suitable and advantageous set of parameter values. These parameter values precisely characterize (define) a very detailed setting possibility for the computed tomography scanner and its software. With this very detailed setting, the individual technical sub-steps of the method, including the automatic analysis of the image data by means of the selected analysis application, are coordinated to one another in a particularly favorable manner, such that the information obtained by means of the analysis application is particularly precise.

This set of parameter values, as a component of a so-called scan protocol, is automatically transmitted in the third procedural step VS3 to the selected medical modality, i.e.

the computed tomography scanner 8, and used there for the presetting of the modality 8. In this manner the computed tomography scanner 8 is configured or parameterized for the upcoming examination.

Through the activation of a button, symbolized by an information flow arrow II, the user, who is trained for working with the selected modality, confirms the presetting parameter values, as a result of which the actual examination of the patient, and thereby the fourth procedural step VS4, is initiated.

In the framework of the fourth procedural step VS4, the generation of raw data takes place with the aid of the computed tomography scanner 8. The raw data are subjected to an image reconstruction in the fifth procedural step VS5, in order to generate image data. The image reconstruction is executed with the use of a software program and a computer, which are components of the computed tomography scanner 8. The image data obtained in this manner are then sent to the central computer unit 4, and stored therein as a file.

Preferably, in addition to the image data, the patient data used as basis data, and the parameter values that were used, are stored in a file of this type. For another follow-up examination, it is possible to read out, in particular, the parameter values from a file of this type, by means of the secondary application, such that the parameter values for another follow-up examination can be re-used, if desired. The files created in this manner, indicated by an information flow arrow III, are sent as a copy to the information storage unit 6, and archived therein. The physician has access to the information storage unit 6, such that he can open the files on his PC at any time and evaluate them.

Depending on the results, the secondary application initiates the analysis application previously selected by the physician in the sixth procedural step VS6, which analyzes the generated image data. In the present case example, this means that the analysis application determines image data that are typical of tumor tissue, that the analysis application also executes a segmenting of the image data in which a coherent image region is determined, which depicts a suspected tumor, and that the analysis application finally, using this depiction of the suspected tumor, undertakes a size determination.

The information determined through the analysis is subsequently stored in the seventh procedural step VS7 either in a separate file, or together with the image data in an extended file, symbolized by an information flow arrow IV, as a copy, by the central computer unit 4, and transmitted to the information storage unit 6.

The information from the analysis is then evaluated by the physician on a PC in the examination room, and used to make a diagnosis of the patient or to verify a diagnosis.

In addition, the physician has the possibility of using the file with the image data on the PC in order to analyze said data with the use of a separate program installed on the PC, using other analysis applications. Accordingly, it is alternatively possible to execute the procedural steps VS6 an VS7 on the physician's PC. When the procedural steps VS6 and VS7 are executed on the PC, the physician is preferably made aware of which analysis application the respective image data are suited for by means of an automatic restriction to the selectable analysis applications. The physician then selects from the restricted selection an analysis application and initiates said application. The corresponding input in the PC is indicated by an information flow arrow V.

An advantageous configuration of apparatuses for the execution of the method 2 is indicated in FIG. 2. A post processing server, such as "syngo.via," (commercially available form Siemens Healthcare) for example, functions thereby as the central computer unit 4. The transmission of the basis information to the post processing server is obtained via a so-called radiology information system 10, abbreviated as RIS 10, that the physician can access from his PC, and with which the physician can process the patient's data. Based on the basis information, the determination of the appropriate set of parameter values is obtained by means of a secondary application executed on the post processing server as a software program, which are then transmitted to the computed tomography scanner 8, in order to configure said scanner. Subsequently, the generation of the raw data and the generation of image data are carried out with the computed tomography scanner 8, with the image data being sent to the post processing server. The image data are archived in a storage 6 with the use of a so-called picture archiving and communication system (PACS) 12, and are then available to the physician in the form of a stored file. Furthermore, the image data or the contents of the display monitor are sent to a so-called post processing client 14, in order to execute the analysis application with the aid of said post processing client. Accordingly, with this configuration, the analysis application is executed using a separate computer, e.g. on a PC in the same room in which the computed tomography scanner 8 is operated. The information obtained from the analysis is then sent to the post processing server, and also archived with PACS 12.

Although modifications and changes may be suggested by those skilled in the art, it is the intention of the inventor to embody within the patent warranted hereon all changes and modifications as reasonably and properly come within the scope of his contribution to the art.

I claim:

1. A method for generating a medical image and evaluating the medical image, comprising:

in a processor comprising a user interface, executing, prior to acquisition of raw data from a patient, a primary application program that formulates a sequence of operation of a medical modality, dependent on selected modality parameters, to operate said medical modality to acquire said raw data from the patient by interaction of the patient with the medical modality, and to operate a reconstruction computer to reconstruct image data from the raw data to produce the medical image by executing a reconstruction algorithm employing selected reconstruction parameters, and to control an automated evaluation of the medical image dependent on a selected analysis application program, wherein said modality parameters and selection of said reconstruction parameters affect an image content of said medical image;

via said interface, entering a designation of the selected analysis application program and a designation of patient information describing at least one physical attribute of the patient that is needed for said automated evaluation of the medical image, said selected analysis application program having an image content requirement that said medical image must satisfy in order for said medical image to be analyzed by said selected analysis application program;

executing a secondary application program in said processor to automatically propose, via said user interface, a single set of parameter values in said sequence for said modality parameters and said reconstruction parameters, said single set of parameter values being coordinated to said analysis application program and the patient information provided to said processor in order to make said medical image satisfy said image content requirement for said analysis application; and presenting a visual representation of the formulated sequence at a display screen in communication with said processor for acceptance or modification by a user.

2. A method as claimed in claim 1 comprising, in said primary application program, presenting the user, via said user interface, with a plurality of analysis application programs in a form allowing said user to select one of said analysis application programs for evaluating said medical image.

3. A method as claimed in claim 2 comprising providing at least one analysis application program, among said plurality of analysis application programs, that is configured to segment said image data in said medical image.

4. A method as claimed in claim 3 wherein said analysis application program configured to segment said image data in said medical image is also configured to automatically analyze the segmented image data.

5. A method as claimed in claim 1 wherein said secondary application program sets said image content requirements selected from the group consisting of contrast and image sharpness.

6. A method as claimed in claim 1 comprising, via said secondary application program, automatically presetting said modality parameters.

7. A method as claimed in claim 1 comprising, via said secondary application program, automatically presetting said reconstruction parameters.

8. A method as claimed in claim 1 comprising employing, as said patient information, patient-specific data describing anatomical or physiological features of the patient.

9. A method as claimed in claim 1 comprising storing data representing a baseline examination in a memory file that is accessible by said processor and, when executing said secondary application program, automatically accessing said data representing said baseline examination from said file and using at least a portion of said data representing said baseline examination as a reference with respect to which said medical image is analyzed, and comprising formulating said single set of parameters for said sequence in order to give said medical image an image content that is consistent with said data representing said baseline examination, in order to allow said data representing said baseline examination to be used as said reference with respect to which said medical image is analyzed.

10. A method as claimed in claim 9 comprising, in said secondary application program, transforming parameter values for said baseline examination, contained in said data representing said baseline information, into a set of parameter values according to a stored algorithm accessible by said processor, in order to make said at least one of said acquisition of said raw data, said reconstruction of said medical image, and said evaluation of said medical image, comparable to said baseline examination.

11. A method as claimed in claim 10 comprising, in said stored algorithm for transforming said parameter values, automatically compensating for anatomical changes to said patient that have occurred between said baseline examination and said acquisition of said raw data from said patient.

12. A method as claimed in claim 10 comprising, in said stored algorithm for transforming said parameter values, automatically compensating for technical changes to said imaging modality that have occurred between said baseline examination and said acquisition of said raw data from said patient.

13. A method as claimed in claim 1 comprising employing a computed tomography apparatus as said medical modality.

* * * * *